(12) United States Patent
Kölling

(10) Patent No.: US 7,465,818 B2
(45) Date of Patent: Dec. 16, 2008

(54) PROCESS FOR THE RACEMOSELECTIVE SYNTHESIS OF ANSA-METALLOCENES

(75) Inventor: Lars Kölling, Mannheim (DE)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 11/629,928

(22) PCT Filed: Jun. 30, 2005

(86) PCT No.: PCT/EP2005/007058

§ 371 (c)(1), (2), (4) Date: Dec. 18, 2006

(87) PCT Pub. No.: WO2006/002924

PCT Pub. Date: Jan. 12, 2006

(65) Prior Publication Data

US 2008/0027239 A1  Jan. 31, 2008

Related U.S. Application Data

(60) Provisional application No. 60/591,574, filed on Jul. 27, 2004.

(30) Foreign Application Priority Data

Jul. 2, 2004  (DE) ........................ 10 2004 032 277

(51) Int. Cl.
*C07F 17/00* (2006.01)
*B01J 31/00* (2006.01)

(52) U.S. Cl. .................... 556/17; 556/18; 556/30; 502/103; 502/155; 526/943

(58) Field of Classification Search ............... 556/17, 556/18, 30; 502/103, 155
See application file for complete search history.

(56) References Cited

U.S. PATENT DOCUMENTS

| 6,133,277 | A | 10/2000 | Wigerinck et al. | ........... 514/274 |
| 6,153,777 | A | 11/2000 | Jordan et al. | ................. 556/11 |
| 2004/0063574 | A1 | 4/2004 | Theopold et al. | ............ 502/150 |

FOREIGN PATENT DOCUMENTS

WO  2004/037840  5/2004

OTHER PUBLICATIONS

R. Gleiter et al., "Zur Reacktion von Bis(trimethylphosphan)titanocen mit Ketonen," *Chem. Ber.*, vol. 127, p. 1797-1798 (1994).

*Primary Examiner*—Porfirio Nazario-Gonzalez
(74) *Attorney, Agent, or Firm*—William R. Reid

(57) ABSTRACT

A process for the racemoselective preparation of ansa-metallocene complexes of the formula (I),

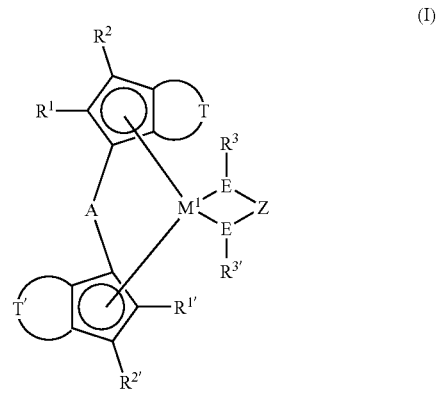

where
$R^1$, $R^{1'}$, $R^2$, $R^{2'}$ are identical or different and are each hydrogen or an organic radical having from 1 to 40 carbon atoms,
$R^3$, $R^{3'}$ are identical or different and are each an organic radical having from 1 to 40 carbon atoms,
T, T' are identical or different and are each a divalent organic group which has from 1 to 40 carbon atoms,
A is a divalent atom or a divalent group,
Z is a divalent atom or a divalent group,
E is P, As or Sb,
$M^1$ is an element of group 4 of the Periodic Table of the Elements,
$M^2$ is an alkali metal, an alkaline earth metal or a magnesium monohalide fragment,
p is 1 or 2.

6 Claims, No Drawings

PROCESS FOR THE RACEMOSELECTIVE SYNTHESIS OF ANSA-METALLOCENES

This application is the U.S. national phase of International Application PCT/EP2005/007058, filed Jun. 30, 2005, claiming priority to German Patent Application 102004032277.5 filed Jul. 2, 2004, and the benefit under 35 U.S.C. 119(e) of U.S. Provisional Application No. 60/591,574, filed Jul. 27, 2004; the disclosures of International Application PCT/EP2005/007058, German Patent Application 102004032277.5 and U.S. Provisional Application No. 60/591,574, each as filed, are incorporated herein by reference.

DESCRIPTION

The present invention relates to a process for the racemoselective preparation of ansa-metallocene complexes of the formula (I), the subsequent conversion of these complexes into ansa-metallocenes of the formula (IV), transition metal compounds of the formula (III) and their use of the racemoselective preparation of ansa-metallocenes, ansa-metallocene complexes of the formula (I) and the use of these as constituents of catalyst systems for the polymerization of olefinically unsaturated compounds.

Research and development on the use of organic transition metal compounds, in particular metallocene, as catalyst components for the polymerization and copolymerization of olefins with the objective of preparing tailored polyolefins has been pursued intensively at universities and in industry over the past 15 years.

Now, both the ethylene-based polyolefins prepared by means of metallocene catalyst systems and, in particular, the propylene-based polyolefins prepared by means of metallocene catalyst systems represent a dynamically growing market segment.

The preparation of isotactic polypropylenes is generally carried out using ansa-metallocenes in their racemic form. In the synthesis of the racemic ansa-metallocenes, they are generally obtained together with the undesired meso-metallocenes which usually have to be separated off. Various diastereoselective syntheses in which the proportion of the desired racemic metallocene is higher than the proportion of the undesired meso form have been developed.

U.S. Pat. No. 6,153,777 describes a process for preparing racemic ansa-zirconocenes, in which a bisanion of a bridged biscyclopentadienyl ligand system is reacted with a specific zirconium source, namely dichlorozirconium N,N'-diphenyl-trimethylenediamide. The chelating diamine is prepared from aniline and 1,3-dibromopropane. Aniline itself is a toxic chemical which endangers the environment.

It was therefore an object of the invention to find a process for the racemoselective preparation of ansa-metallocene complexes which offers advantage both from an economic point of view and in respect of the environment-related properties of the starting materials used.

We have accordingly found a process for the racemoselective preparation of ansa-metallocene complexes of the formula (I),

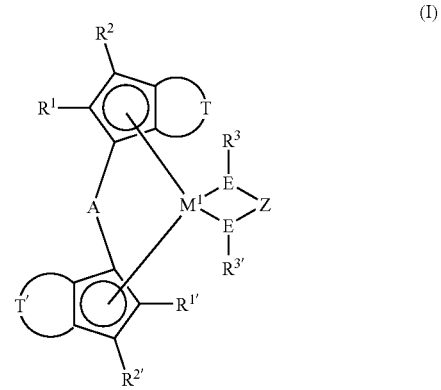

which comprises reacting a ligand starting compound of the formula (II)

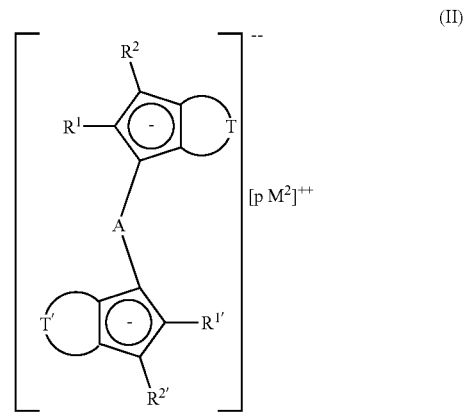

with a transition metal compound of the formula (III)

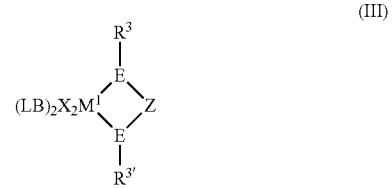

where
$R^1$, $R^{1'}$ are identical or different and are each hydrogen or an organic radical having from 1 to 40 carbon atoms,
$R^2$, $R^{2'}$ are identical or different and are each hydrogen or an organic radical having from 1 to 40 carbon atoms,
$R^3$, $R^{3'}$ are identical or different and are each an organic radical having from 1 to 40 carbon atoms,
T, T' are identical or different and are each a divalent organic group which has from 1 to 40 carbon atoms and together with the cyclopentadienyl ring forms at least one further saturated or unsaturated, substituted or unsubstituted ring system which has a ring size of from 5 to 12 atoms, where T and T' may contain the heteroatoms Si, Ge, N, P, As, Sb, O, S, Se or Te within the ring system fused to the cyclopentadienyl ring, A is a bridge consisting of a divalent atom or a divalent group,
Z is a bridge consisting of a divalent atom or a divalent group,
E is P, As or Sb,
$M^1$ is an element of group 4 of the Periodic Table of the Elements,
$M^2$ is an alkali metal, an alkaline earth metal or a magnesium monohalide fragment,
p is 1 in the case of doubly positively charged metal ions or is 2 in the case of singly positively charged metal ions or metal ion fragments,
the radicals X are identical or different and are each an organic or inorganic radical which can be substituted by a cyclopentadienyl anion,
and
LB is an uncharged Lewis-base ligand.

The radicals $R^1$ and $R^{1'}$ are identical or different, preferably identical, and are each hydrogen or an organic radical having from 1 to 40 carbon atoms, for example $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl having from 1 to 10, preferably from 1 to 4, carbon atoms in the alkyl radical and from 6 to 22, preferably from 6 to 10, carbon atoms in the aryl radical, or a $C_2$-$C_{40}$-heteroaromatic radical containing at least one heteroatom selected from the group consisting of the elements O, N, S, P and Se, in particular O, N and S, where the heteroaromatic radical may be substituted by further radicals $R^6$, where $R^6$ is an organic radical having from 1 to 20 carbon atoms, for example $C_1$-$C_{10}$-, preferably $C_1$-$C_4$-alkyl, $C_6$-$C_{15}$-, preferably $C_6$-$C_{10}$-aryl, alkylaryl, arylalkyl, fluoroalkyl or fluoroaryl each having from 1 to 10, preferably from 1 to 4, carbon atoms in the alkyl radical and from 6 to 18, preferably from 6 to 10, carbon atoms in the aryl radical, and a plurality of radicals $R^6$ may be identical or different. Preference is given to $R^1$ and $R^{1'}$ being identical or different, preferably identical, and each being $C_1$-$C_{10}$-alkyl such as methyl, ethyl, n-propyl, isopropyl, n-butyl, i-butyl, s-butyl, t-butyl, n-pentyl, cyclopentyl, n-hexyl, cyclohexyl, n-heptyl or n-octyl, preferably methyl, ethyl or isopropyl, in particular methyl.

The radicals $R^2$ and $R^{2'}$ are identical or different, preferably identical, and are each hydrogen or an organic radical having from 1 to 40 carbon atoms, for example $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl each having from 1 to 10, preferably from 1 to 4, carbon atoms in the alkyl radical and from 6 to 22, preferably from 6 to 10, carbon atoms, in the aryl radical, or a $C_2$-$C_{40}$-heteroaromatic radical containing at least one heteroatom selected from the group consisting of the elements O, N, S, P and Se, in particular O, N and S, where the heteroaromatic radical may be substituted by further radicals $R^6$, as defined above, and a plurality of radicals $R^6$ may be identical or different. $R^2$ and $R^{2'}$ are preferably each hydrogen.

The radicals $R^3$ and $R^{3'}$ are identical or different, preferably identical, and are each an organic radical having from 1 to 40 carbon atoms, for example $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl having from 1 to 10, preferably from 1 to 4, carbon atoms in the alkyl radical and from 6 to 22, preferably from 6 to 10, carbon atoms in the aryl radical, or a $C_2$-$C_{40}$-heteroaromatic radical containing at least one heteroatom selected from the group consisting of the elements O, N, S, P and Se, in particular O, N and S, where the heteroaromatic radical may be substituted by further radicals $R^6$, as defined above, and a plurality of radicals $R^6$ may be identical or different. Preference is given to the radicals $R^3$ and $R^{3'}$ being identical and each being a $C_6$-$C_{10}$-aryl radical or a $C_7$-$C_{14}$-alkylaryl radical. Examples of particularly preferred radicals $R^3$ and $R^{3'}$ are phenyl, 1-naphthyl, 3,5-dimethylphenyl and p-tert-butylphenyl.

T and T' are identical or different, preferably identical, and are each a divalent organic group which has from 1 to 40 carbon atoms and together with the cyclopentadienyl ring forms at least one further saturated or unsaturated, substituted or unsubstituted ring system which has a ring size of from 5 to 12, in particular from 5 to 7, atoms, where T and T' may contain the heteroatoms Si, Ge, N, P, As, Sb, O, S, Se or Te, preferably Si, N, O or S, in particular S or N, within the ring system fused to the cyclopentadienyl ring.

Examples of preferred divalent organic groups T or T' are

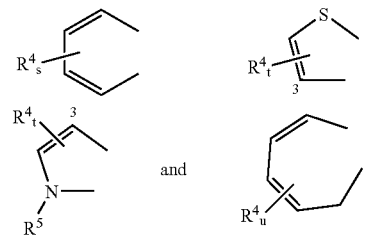

preferably

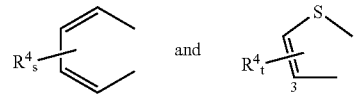

in particular

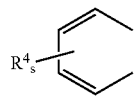

where the radicals $R^4$ are identical or different and are each an organic radical having from 1 to 40, preferably from 1 to 20, carbon atoms, for example a cyclic, branched or unbranched $C_1$-$C_{20}$-, preferably $C_1$-$C_8$-alkyl radical, a $C_2$-$C_{20}$-, preferably $C_2$-$C_8$-alkenyl radical, a $C_6$-$C_{22}$-, preferably $C_6$-$C_{10}$-aryl radical, an alkylaryl or arylalkyl radical having from 1 to 10, preferably from 1 to 4, carbon atoms in the alkyl radical and from 6 to 22, preferably from 6 to 10, carbon atoms in the aryl radical, where the radicals may also be halogenated, or the radical $R^4$ is a substituted or unsubstituted, saturated or unsaturated, in particular aromatic heterocyclic radical which has from 2 to 40, in particular from 4 to 20, carbon atoms and contains at least one heteroatom, preferably selected from the group of elements consisting of O, N, S and P, in particular O, N and S, or two adjacent radicals $R^4$ together with the atoms connecting them form a monocyclic or polycyclic, substituted or unsubstituted ring system which has from 1 to 40 carbon atoms and may also contain heteroatoms selected from the group consisting of the elements Si, Ge, N, P, O, S, Se and Te, in particular N and S, $R^5$ is hydrogen or is as defined for $R^4$, s is a natural number from 0 to 4, in particular from 0 to 3, t is a natural number from 0 to 2, in particular 1 or 2, and u is a natural number from 0 to 6, in particular 1.

A is a bridge consisting of a divalent atom or a divalent group. Examples of A are:

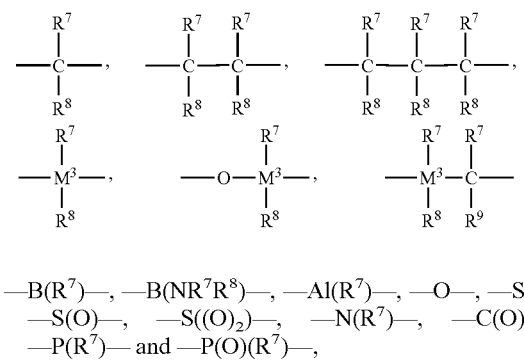

$-B(R^7)-$, $-B(NR^7R^8)-$, $-Al(R^7)-$, $-O-$, $-S-$, $-S(O)-$, $-S((O)_2)-$, $-N(R^7)-$, $-C(O)-$, $-P(R^7)-$ and $-P(O)(R^7)-$, in particular

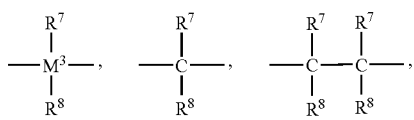

where $M^3$ is silicon, germanium or tin, preferably silicon or germanium, particularly preferably silicon, and $R^7$, $R^8$ and $R^9$ are identical or different and are each a hydrogen atom, a halogen atom, a trimethylsilyl group, a $C_1$-$C_{10}$-, preferably $C_1$-$C_3$-alkyl group, a $C_1$-$C_{10}$-fluoroalkyl group, a $C_6$-$C_{10}$-fluoroaryl group, a $C_6$-$C_{10}$-aryl group, a $C_1$-$C_{10}$-, preferably $C_1$-$C_3$-alkoxy group, a $C_7$-$C_{15}$-alkylaryloxy group, a $C_2$-$C_{10}$-, preferably $C_2$-$C_4$-alkenyl group, a $C_7$-$C_{40}$-arylalkyl group, a $C_8$-$C_{40}$-arylalkenyl group or a $C_7$-$C_{40}$-alkylaryl group or two adjacent radicals together with the atoms connecting them form a saturated or unsaturated ring having from 4 to 15 carbon atoms.

Preferred embodiments of A are the bridges:

dimethylsilanediyl, methylphenylsilanediyl, methyl-tert-butyl-silanediyl, diphenylsilanediyl, dimethylgermanediyl, ethylidene, 1-methylethylidene, 1,1-dimethylethylidene, 1,2-dimethylethylidene, 1,1,2,2-tetramethylethylidene, dimethylmethylidene, phenylmethylmethylidene or diphenylmethylidene, in particular dimethylsilanediyl, diphenylsilanediyl and ethylidene.

A is particularly preferably a substituted silylene group or a substituted or unsubstituted ethylene group, preferably a substituted silylene group such as dimethylsilanediyl, methylphenylsilanediyl, methyl-tert-butylsilanediyl or diphenylsilanediyl, in particular dimethylsilanediyl.

Z is a bridge consisting of a divalent atom or a divalent group, Z is preferably a 1,3-trimethylene unit.

E is P, As or Sb, preferably P.

$M^1$ is an element of group 4 of the Periodic Table of the Elements, e.g. titanium, zirconium or hafnium, preferably zirconium or hafnium, particularly preferably zirconium.

$M^2$ is an alkali metal such as Li, Na or K, an alkaline earth metal such as Mg or Ca, in particular Mg, or a magnesium monohalide fragment such as MgCl, MgBr or MgI. $M^2$ is preferably Li, Na, K, MgCl, MgBr, MgI or Mg, particularly preferably Li, K or Mg, in particular Li.

p is 1 in the case of doubly positively charged metal ions or is 2 in the case of singly positively charged metal ions or metal ion fragments.

The radicals X are identical or different, preferably identical, and are each an organic or inorganic radical which can be substituted by a cyclopentadienyl anion. Examples of X are halogen such as chlorine, bromine, iodine, in particular chlorine, organosulfonate groups such as trifluoromethanesulfonate (triflate) or mesylate. X is preferably halogen, in particular chlorine.

LB is an uncharged Lewis-base ligand, preferably a linear, cyclic or branched oxygen-, sulfur-, nitrogen- or phosphorus-containing hydrocarbon, in particular an oxygen- or nitrogen-containing hydrocarbon, for example an ether, polyether, thioether, amine, polyamine or phosphine. LB is preferably a cyclic or acyclic ether or diether such as diethyl ether, dibutyl ether, tert-butyl methyl ether, anisole, dimethoxyethane (DME), tetrahydrofuran (THF) or dioxane. Particular preference is given to THF or DME.

Furthermore, the substituents described according to the present invention are, unless restricted further, defined as follows:

The term "organic radical having from 1 to 40 carbon atoms" as used in the present text refers, for example, to $C_1$-$C_{40}$-alkyl radicals, $C_1$-$C_{10}$-fluoroalkyl radicals, $C_1$-$C_{12}$-alkoxy radicals, saturated $C_3$-$C_{20}$-heterocyclic radicals, $C_6$-$C_{40}$-aryl radicals, $C_2$-$C_{40}$-heteroaromatic radicals, $C_6$-$C_{10}$-fluoroaryl radicals, $C_6$-$C_{10}$-aryloxy radicals, $C_3$-$C_{18}$-trialkylsilyl radicals, $C_2$-$C_{20}$-alkenyl radicals, $C_2$-$C_{20}$-alkynyl radicals, $C_7$-$C_{40}$-arylalkyl radicals or $C_8$-$C_{40}$-arylalkenyl radicals. An organic is in each case derived from an organic compound. Thus, the organic compound methanol can in principle give rise to three different organic radicals having one carbon atom, namely methyl ($H_3C-$), methoxy ($H_3C-O-$) and hydroxymethyl ($HOC(H_2)-$).

The term "alkyl" as used in the present text encompasses linear or singly or multiply branched saturated hydrocarbons which may also be cyclic. Preference is given to $C_1$-$C_{18}$-alkyl, such as methyl, ethyl, n-propyl, n-butyl, n-pentyl, n-hexyl, n-heptyl, n-octyl, n-nonyl, n-decyl, cyclopentyl, cyclohexyl, isopropyl, isobutyl, isopentyl, isohexyl, sec-butyl or tert-butyl.

The term "alkenyl" as used in the present text encompasses linear or singly or multiply branched hydrocarbons having one or more C-C double bonds which may be cumulated or alternating.

The term "saturated heterocyclic radical" as used in the present text refers, for example, to monocyclic or polycyclic, substituted or unsubstituted hydrocarbon radicals in which one or more carbon atoms, CH groups and/or $CH_2$ groups have been replaced by heteroatoms, preferably selected from the group consisting of O, S, N and P. Preferred examples of substituted or unsubstituted saturated heterocyclic radicals are pyrrolidinyl, imidazolidinyl, pyrazolidinyl, piperidyl, piperazinyl, morpholinyl, tetrahydrofuranyl, tetrahydropyranyl, tetrahydrothiophenyl and the like, and also methyl-, ethyl-, propyl-, isopropyl- and tert-butyl-substituted derivatives thereof.

The term "aryl" as used in the present text refers, for example, to aromatic and if appropriate also fused polyaromatic substituents which may optionally be monosubstituted or polysubstituted by linear or branched $C_1$-$C_{18}$-alkyl, $C_1$-$C_{18}$-alkoxy, $C_2$-$C_{10}$-alkenyl or halogen, in particular fluorine. Preferred examples of the substituted or unsubstituted aryl radicals are, in particular, phenyl, pentafluorophenyl, 4-methylphenyl, 4-ethylphenyl, 4-n-propylphenyl, 4-isopropylphenyl, 4-tert-butylphenyl, 4-methoxyphenyl, 1-naphthyl, 9-anthryl, 9-phenanthryl, 3,5-dimethylphenyl, 3,5-di-tert-butylphenyl or 4-trifluoromethylphenyl.

The term "heteroaromatic radical" as used in the present text refers, for example, to aromatic hydrocarbon radicals in which one or more carbon atoms have been replaced by nitrogen, phosphorus, oxygen or sulfur atoms or combinations thereof. These can, like the aryl radicals, optionally be monosubstituted or polysubstituted by linear or branched $C_1$-$C_{18}$-alkyl, $C_2$-$C_{10}$-alkenyl or halogen, in particular fluorine. Preferred examples are furyl, thienyl, pyrrolyl, pyridyl, pyrazolyl, imidazolyl, oxazolyl, thiazolyl, pyrimidinyl, pyrazinyl and the like, and also methyl-, ethyl-, propyl-, isopropyl- and tert-butyl-substituted derivatives thereof.

The term "arylalkyl" as used in the present text refers, for example, to aryl-containing substituents whose aryl radical is linked via an alkyl chain to the remainder of the molecule. Preferred examples are benzyl, substituted benzyl, phenethyl, substituted phenethyl and the like.

Fluoroalkyl and fluoroaryl are substituents in which at least one hydrogen atom, preferably more than one and a maximum of all hydrogen atoms, have been replaced by fluorine atoms. Examples of fluorine-containing substituents which are preferred according to the invention are trifluoromethyl, 2,2,2-trifluoroethyl, pentafluorophenyl, 4-trifluoromethylphenyl, 4-perfluoro-tert-butylphenyl and the like.

In a preferred embodiment of the process of the invention, the metallocene complex of the formula (I) is reacted with suitable elimination reagents in a subsequent reaction step to form an ansa-metallocene complex of the formula (IV)

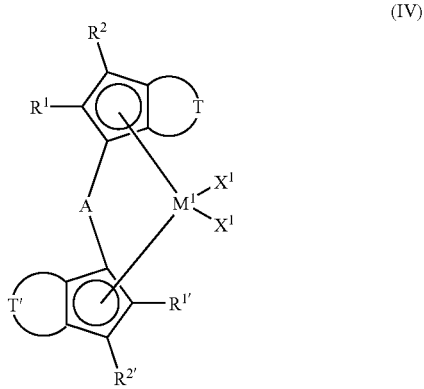

(IV)

where the radicals $X^1$ are identical or different and are each methyl or halogen, for example fluorine, chlorine, bromine or iodine, in particular chlorine.

The present invention therefore also provides for the use of an ansa-metallocene complex of the formula (I) as intermediate for the preparation of ansa-metallocene complexes of the formula (IV).

Elimination reagents are known in principle. Examples of preferred elimination reagents are hydrogen halides such as HCl and also aliphatic or aromatic carboxylic acid halides such as acetyl chloride, acetyl bromide, phenylacetyl chloride, tert-butylacetyl chloride, and also organoaluminum halides such as ethylaluminum dichloride, methylaluminum dichloride or dimethylaluminum chloride, or halogen-containing main group compounds such as $SiCl_4$, $SOCl_2$, $PCl_5$ or $AlCl_3$.

Particularly preferred elimination reagents are HCl, acetyl chloride, ethylaluminum dichloride and methylaluminum dichloride.

The elimination reaction is usually carried out in a temperature range from 0° C. to 110° C. To complete the reaction, use is normally made of at least stoichiometric amounts of the elimination reagent, with excess elimination reagent generally not causing any problems as long as it can be separated off without problems from the target product in the work-up.

Particular preference is given to a process for the racemoselective preparation of ansa-metallocene complexes of the formula (I), optionally comprising the subsequent conversion of these complexes into ansa-metallocenes of the formula (IV), where $R^3$, $R^{3'}$ are identical and are each a $C_6$-$C_{10}$-aryl radical or a $C_7$-$C_{14}$-alkylaryl radical, in particular phenyl, 1-naphthyl, 3,5-dimethylphenyl or p-tert-butylphenyl.

Z is a 1,3-trimethylene unit,

E is P, $M^1$ is Zr or Hf, in particular Zr, the radicals X are identical and are each chlorine and LB is tetrahydrofuran or two ligands LB represent dimethoxyethane.

In the process of the invention, the salt-like ligand starting compounds of the formulae (II) can be used either in isolated form or they can be prepared in situ immediately prior to the reaction with the transition metal compound of the formula (III).

To synthesize the salt-like ligand starting compounds of the formula (II), the corresponding uncharged bridged biscyclopentadienyl compound is usually doubly deprotonated by means of a strong base. As strong bases, it is possible to use, for example, organometallic compounds or metal hydrides, preferably compounds containing an alkali metal or an alkaline earth metal. Preferred bases are organolithium or organomagnesium compounds such as methyllithium, n-butyllithium, sec-butyllithium, n-butyl-n-octylmagnesium or dibutylmagnesium.

The uncharged bridged biscyclopentadienyl compound to be deprotonated can once again be used in isolated form or without isolation, directly from the bridging reaction of two cyclopentadienyl anions with an appropriate bridging reagent, for example a diorganodichlorosilane such as dimethyldichlorosilane. A further possible way of preparing the uncharged biscyclopentadienyl compounds is stepwise assembly. Here, for example, a cyclopentadienyl anion is firstly reacted with an appropriate bridging reagent, for example a diorganodichlorosilane such as dimethyldichlorosilane, to form a monochloromonocyclopenta-dienyidiorganosilane compound and the chlorine in this is subsequently replaced by a further cyclopentadienyl radical, which may be different from the first, to give the desired uncharged bridged biscyclopentadienyl compound.

The synthesis of the cyclopentadienyl anions can in principle be carried out under the same conditions as the deprotonation of the uncharged bridged biscyclopentadienyl compound.

The double deprotonation of the uncharged bridged biscyclopentadienyl compound to form the ligand starting compound of the formula (II) is usually carried out in the temperature range from −78° C. to 110° C., preferably from 0° C. to 80° C. and particularly preferably from 20° C. to 70° C.

Suitable inert solvents in which the deprotonation of the cyclopentadienyl derivatives by means of strong bases can be carried out are aliphatic or aromatic hydrocarbons such as benzene, toluene, xylene, mesitylene, ethylbenzene, cumene, decalin, tetralin, pentane, hexane, cyclohexane, heptane or ethers such as diethyl ether, di-n-butyl ether, tert-butyl methyl ether (MTBE), tetrahydrofuran (THF), 1,2-dimethoxyethane (DME), anisole, triglyme, dioxane and also mixtures of these substances. Preference is given to solvents or solvent mixtures in which the subsequent process of the invention for preparing the metallocene complexes of the formula (I) can also be carried out directly.

The synthesis of the transition metal compounds of the formula (III) can be carried out by synthetic methods analogous to those known in principle from the literature. For example, a tetrahalide $M^1X_4$ can be reacted with the salt of the bisanion $(R^3—E—Z—E—R^{3'})^{2-}$ with elimination of two halide ions in an inert solvent, forming the transition metal compound of the formula (III).

The process of the invention allows the reaction of the ligand starting compound of the formula (II) with the transition metal compound of the formula (III) to be carried out in an inert solvent or solvent mixture in a temperature range from −78° C. to 150° C., in particular from 0° C. to 110° C. The inert solvents or solvent mixtures which can be used are preferably the same ones in which the synthesis of the ligand starting compound of the formula (II) has been carried out. The reaction times are usually at least 10 minutes, in general from 1 to 8 hours.

The present invention further provides transition metal compounds of the formula (III)

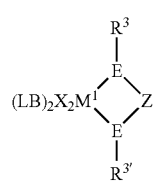

(III)

where the variables and indices are as described above, and the use of the transition metal compounds of the formula (III) for the racemoselective preparation of ansa-metallocene complexes of the formula (I) or the formula (IV) by the process of the invention.

Particular preference is given to compounds of the formula (III) in which $R^3$, $R^{3'}$ are identical and are each a $C_6$-$C_{10}$-aryl radical or a $C_7$-$C_{14}$-alkylaryl radical, Z is a 1,3-trimethylene unit, E is P, $M^1$ is Zr or Hf, the radicals X are identical and are each chlorine and LB is tetrahydrofuran or two ligands LB represent dimethoxyethane.

The process of the invention can form not only the desired rac compounds of the formula (I) but also the corresponding meso compounds, where the terms rac and meso refer only to the spatial arrangement of the two cyclopentadienyl ring systems relative to one another. For example, in cases in which the two cyclopentadienyl radicals on the bridge are not identical, there exists no rac form having $C_2$ symmetry or meso form having $C_s$ symmetry, but there are only diastereomeric compounds having $C_1$ symmetry. These different diastereomeric metallocene compounds which differ in the spatial arrangement of the different substituents when used as catalyst component in the polymerization of propylene behave either like the $C_2$-symmetric rac isomer (isotactic polypropylene) or like the $C_s$-symmetric meso isomer (atactic polypropylene) depending solely on the spatial arrangement of the two cyclopentadienyl ligands relative to one another and can therefore be considered to be a pseudo-rac form or a pseudo-meso form.

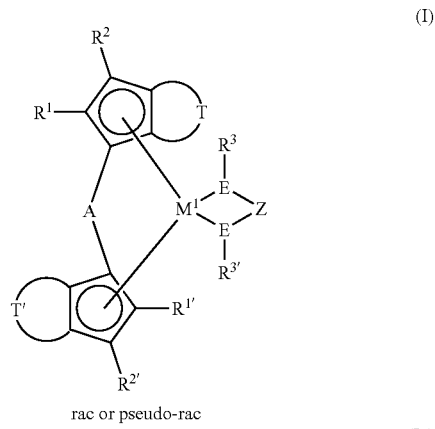

rac or pseudo-rac

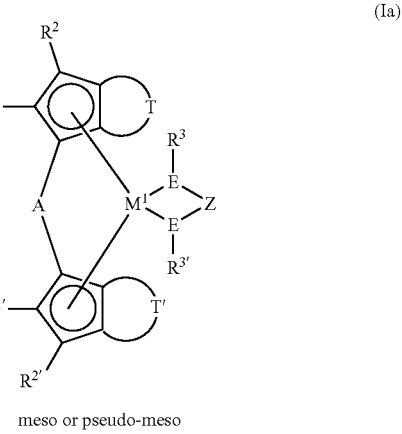

meso or pseudo-meso

In the following, rac and pseudo-rac form or meso and pseudo-meso form are distinguished only as rac and meso form.

Furthermore, in the process of the invention, the rac selectivity=(proportion of rac−proportion of meso)/(proportion of rac+proportion of meso) is greater than zero, preferably greater than 0.5.

The salts of the formulae $M^2X$ or $M^2X_2$, for example lithium chloride or magnesium chloride, which are formed as further reaction product in the process of the invention for preparing racemic ansa-metallocenes of the formula (I) can be separated off from the metallocene by known methods. For example, a salt such as lithium chloride can be precipitated by means of a suitable solvent in which the metallocene is, however, soluble, so that the solid lithium chloride is separated off from the dissolved metallocene by means of a filtration step. The metallocene can also be separated off from the salt by extraction with a suitable solvent of this type. It is also possible to use filtration aids such as kieselguhr in any filtration steps. For example, organic solvents, in particular organic aprotic, oxygen-free solvents such as toluene, ethylenebenzene, xylenes or methylene chloride, are suitable for such a filtration or extraction step. Prior to the above-described removal of a salt, the solvent constituents in which the salt is at least partly soluble may be very substantially removed. For example, lithium chloride has an appreciable solubility in tetrahydrofuran. For this reason, the salts of the formula $M^2X$ or $M^2X_2$ can, as an alternative, also be removed with the aid of a solvent or solvent mixture in which they are readily soluble, while the metallocene complex has a low solubility therein.

The ansa-metallocene complexes of the formula (I) prepared by the process of the invention can be used together with suitable cocatalysts and, if appropriate, suitable support materials as constituents of a catalyst system for the polymerization of olefins.

The present invention further provides ansa-metallocene complexes of the formula (I)

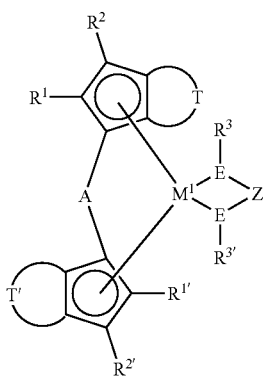

as can be obtained by the process of the invention and the use of an ansa-metallocene complex of the formula (I) as constituent of a catalyst system for the polymerization of olefinically unsaturated compounds.

Preference is given to metallocene complex mixtures which comprise more than 50 mol % of metallocenes of the formula (I) and less than 50 mol % of metallocenes of the formula (Ia), based on the total amount of metallocene compounds, and can be obtained directly by the process of the invention. Particular preference is given to mixtures which comprise more than 75 mol % of metallocenes of the formula (I) and less than 25 mol % of metallocenes of the formula (Ia).

The invention is illustrated by the following nonrestrictive examples:

EXAMPLES

General Procedures

The synthesis and handling of the organometallic compounds and the catalysts was carried out in the absence of air and moisture under argon (glove box and Schienk technique).

Example 1

Synthesis of dilithio-P,P'-diphenyltrimethylenephosphide (1)

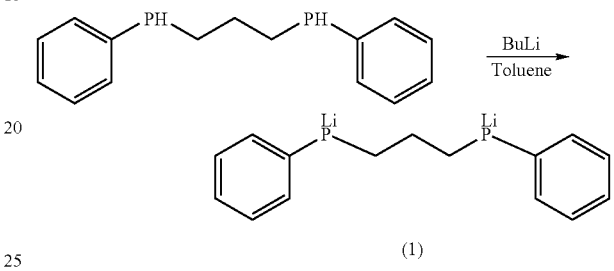

2.00 g (7.68 mmol) of P,P-diphenyltrimethylenephosphine (commercially available) were dissolved in 30 ml of toluene. The solution was cooled to 0° C. and 6.9 ml (17.2 mmol) of a 2.5 M solution of n-butyllithium in hexane were added dropwise at this temperature. The reaction mixture was stirred at room temperature for 18 hours and the reaction product was isolated by filtration. After washing with 2×5 ml of toluene, the product was freed of remaining solvent at $10^{-3}$ mbar. This gave 1.88 g (6.91 mmol) of the dilithio salt (1) in a yield of 90%.

Example 2

Synthesis of dichlorozirconium-P,P'-diphenyltrimethylenediphosphide (2)

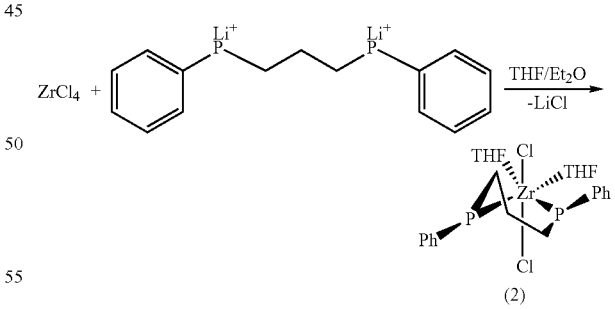

0.78 g (3.33 mmol) of dilithio-P,P'-diphenyltrimethylenediphosphide (1) and 0.91 g (3.34 mmol) of $ZrCl_4$ were cooled to −78° C. Firstly 35 ml of THF and then 35 ml of diethyl ether were added slowly. The reaction mixture was stirred at room temperature for 18 hours and the solvents were subsequently distilled off under reduced pressure. The residue was mixed with 10 ml of toluene and the solvent was subsequently distilled off under reduced pressure. This gave 1.87 g (3.33 mmol) of the compound (2).

Example 3

Synthesis of rac-Me$_2$Si(2-Me-4(4'-t-BuPh)Ind)$_2$ZrCl$_2$ (3)

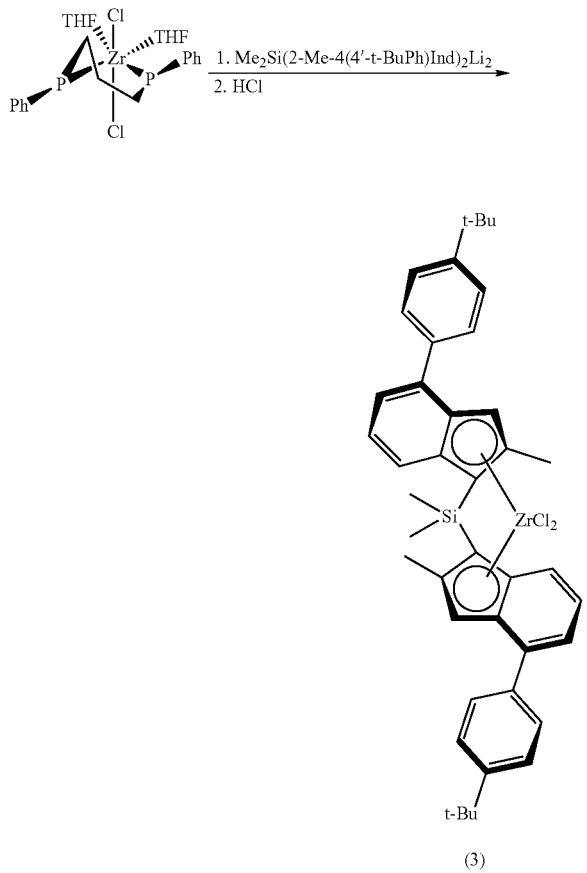

(3)

60 ml of diethyl ether were added dropwise at −78° C. to 1.90 g (3.33 mmol) of Me$_2$Si(2-Me-4(4'-t-BuPh)Ind)$_2$Li$_2$, which had been prepared as a solid by reacting 2.04 g (3.51 mmol) of Me$_2$Si(2-Me-4(4'-t-BuPh)Ind-H)$_2$ with 3.0 ml (7.5 mmol) of a solution of n-butyllithium in hexane (2.5 molar) in diethyl ether and subsequently removing the solvent under reduced pressure, and 1.87 (3.33 mmol) of dichlorozirconium-P,P'-diphenyltrimethylenediphosphide*2 THF (2). The mixture was subsequently stirred at room temperature for 18 hours. The solvent was distilled off under reduced pressure and 60 ml of toluene were added. The mixture was stirred at room temperature for 3 hours and subsequently filtered. The filtrate was cooled to −78° C. and admixed with 7.3 ml (7.3 mmol) of a hydrochloric acid solution (1 M in diethyl ether). The mixture was subsequently stirred for 30 minutes at −78° C. and then for 20 minutes at room temperature. The reaction mixture was once again cooled to −78° C. and the yellow product which precipitated was isolated by filtration. This gave 1.18 g (1.59 mmol) of metallocenes (3) in a yield of 48%.

The invention claimed is:

1. A process for the racemoselective preparation of ansa-metallocene complexes of the formula (I),

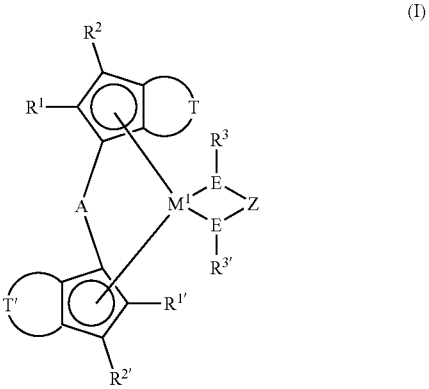

which comprises reacting a ligand starting compound of the formula (II)

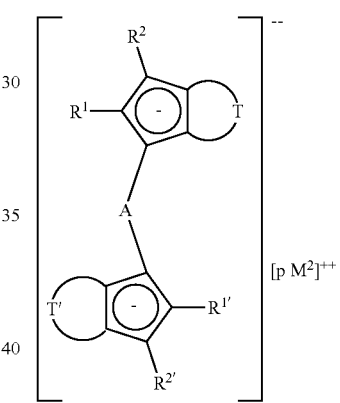

with a transition metal compound of the formula (III)

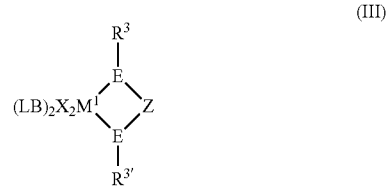

where
- R$^1$, R$^{1'}$ are identical or different and are each hydrogen or an organic radical having from 1 to 40 carbon atoms,
- R$^2$, R$^{2'}$ are identical or different and are each hydrogen or an organic radical having from 1 to 40 carbon atoms,
- R$^3$, R$^{3'}$ are identical or different and are each an organic radical having from 1 to 40 carbon atoms,
- T, T' are identical or different and are each a divalent organic group which has from 1 to 40 carbon atoms and together with the cyclopentadienyl ring forms at least one further saturated or unsaturated, substituted or unsubstituted ring system which has a ring size of from 5 to 12 atoms, where T and T' may contain the heteroatoms Si, Ge, N, P, As, Sb, O, S, Se or Te within the ring system fused to the cyclopentadienyl ring, A is a bridge consisting of a divalent atom or a divalent group, Z is a bridge consisting of a divalent atom or a divalent group, E is P, As or Sb, $M^1$ is an element of group 4 of the Periodic Table of the Elements, $M^2$ is an alkali metal, an alkaline earth metal or a magnesium monohalide fragment, p is 1 in the case of doubly positively charged metal ions or is 2 in the case of singly positively charged metal ions or metal ion fragments, the radicals X are identical or different and are each an organic or inorganic radical which can be substituted by a cyclopentadienyl anion, and LB is an uncharged Lewis-base ligand.

2. The process according to claim 1, wherein the metallocene complex of the formula (I) is reacted with suitable elimination reagents in a subsequent reaction step to form an ansa-metallocene complex of the formula (IV)

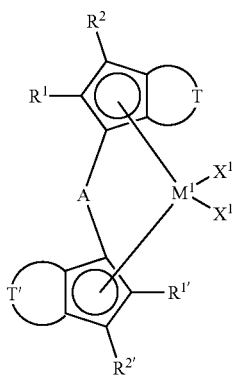

(IV)

where the radicals $X^1$ are identical and are each methyl or halogen.

3. The process according to claim 1 or 2, wherein $R^3$, $R^{3'}$ are identical and are each a $C_6$-$C_{10}$-aryl radical or a $C_7$-$C_{14}$-alkylaryl radical, Z is a 1,3-trimethylene unit, E is P, $M^1$ is Zr or Hf, the radicals X are identical and are each chlorine and LB is tetrahydrofuran or two ligands LB represent dimethoxyethane.

4. A transition metal compound of the formula (III)

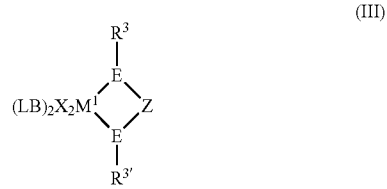

(III)

where the variables and indices are as defined in claim 1.

5. An ansa-metallocene complex of the formula (I)

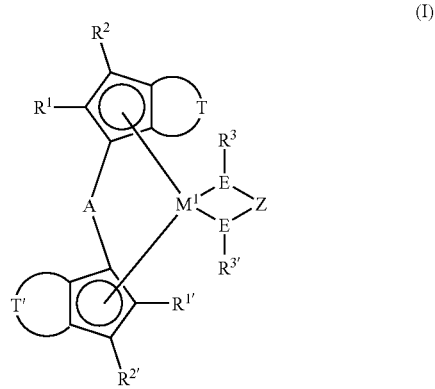

(I)

where the variables and indices are as defined in claim 1.

6. The use of an ansa-metallocene complex of the formula (I) as constituent of catalyst systems for the polymerization of olefinically unsaturated compounds.

* * * * *